United States Patent [19]
Kricka

[11] Patent Number: 5,629,168
[45] Date of Patent: May 13, 1997

[54] CHEMILUMINESCENT ENHANCERS

[75] Inventor: Larry J. Kricka, Berwyn, Pa.

[73] Assignee: British Technology Group Limited, London, England

[21] Appl. No.: 478,336

[22] Filed: Jun. 7, 1995

Related U.S. Application Data

[63] Continuation of Ser. No. 157,504, Nov. 26, 1993, abandoned, which is a continuation of Ser. No. 925,689, Aug. 7, 1992, abandoned, which is a continuation-in-part of Ser. No. 833,153, Feb. 10, 1992, abandoned.

[51] Int. Cl.[6] ............................. C12Q 1/28; C12Q 1/26; C12Q 1/00; G01N 33/566
[52] U.S. Cl. ..................... 435/28; 435/25; 435/27; 435/24; 435/7.94; 435/7.93; 435/810; 435/975; 435/4; 436/501; 436/546; 436/808; 436/63; 558/287; 558/286
[58] Field of Search ............................. 435/28, 25, 27, 435/24, 7.94, 7.93, 810, 975, 4; 436/501, 546, 808, 63; 558/287, 286

[56] References Cited

U.S. PATENT DOCUMENTS

| | | | |
|---|---|---|---|
| 4,868,130 | 9/1989 | Hargreaves | 435/7.94 |
| 4,950,613 | 8/1990 | Arnold, Jr. et al. | 436/546 |

FOREIGN PATENT DOCUMENTS

| | | |
|---|---|---|
| 342024A | 11/1989 | European Pat. Off. . |
| 2162946 | 2/1986 | United Kingdom . |
| WO91/05872 | 5/1991 | WIPO . |

OTHER PUBLICATIONS

Burnett et al, Biochemical & Biophysical Research Comm, vol. 96, No. 1, pp. 157–162, (1980).

G.H. Thorpe and L.J. Kricka, "Enhanced Chemiluminescent Reactions Catalyzed by Horseradish Peroxidase", Methods in Enzymology 133, 331–353 (1986).

R.A. Bowie and O.C. Musgrave, "Organoboron compounds. Part VII ... ", J. Chem Soc. (C), 485–488 (1970).

"Chemiluminescence Principles and Applications in Biology and Medicine" by A.K. Campbell, Ellis Horwood Ltd., 1988, pp. 81 and 82.

"Clinical and Biochemical Luminescence," Ed. L.J. Kricka and T.J.N. Carter, Marcel Decker, 1982, pp.1 and 2.

"Advanced Organic Chemistry" by Jerry March, 4th ed., 1992 at pp. 231–238.

Primary Examiner—John Kight
Assistant Examiner—Louise N. Leary
Attorney, Agent, or Firm—Nixon & Vanderhye

[57] ABSTRACT

Method of increasing the light output and/or signal:background ratio of light output from a chemiluminescent reaction of a dihydrophthalazinedione, a peroxidase enzyme catalyst and an oxidant, by carrying out the reaction in the presence of an enhancer which is an aromatic organo boron compound. Kits suitable for use in diagnositc assays comprising such enhancers are also described.

20 Claims, 3 Drawing Sheets

CHEMILUMINESCENT ENHANCERS

This is a continuing application from Ser. No. 08/157,504 ; filed Nov. 26, 1993, abandoned which is a continuing application from application Ser. No. 07/925,689 filed Aug. 7, 1992, abandoned, which is a continuation-in-part application of Ser. No. 07/833,153 filed Feb. 10, 1992, abandoned.

BACKGROUND OF THE INVENTION

1. Field of the Invention

The present invention relates to an enhanced chemiluminescent reaction especially for use in a diagnostic assay, particularly immunoassay, and to a diagnostic kit for use in the assay. A chemiluminescent reaction is a chemical reaction which results In the emission of light. The luminescent emission is generally of sufficient duration to enable the light emitted to be detected or measured, and thereby to allow the detection or quantification of an analyte. The chemiluminescent reaction with which this invention is concerned is that between a 2,3-dihydro-1,4-phthalaztnedione (DPD), especially luminol, with an oxidant, especially hydrogen peroxide, and a peroxidase enzyme, especially horseradish peroxidase, which catalyses the oxidation of the DPD by the oxidant. The oxidation is accompanied by emission of light.

2. Description of the Prior Art

Luminescent assays making use of the above-mentioned peroxidase-catalysed oxidation of a DPD include several types. This invention is concerned primarily with those in which the presence or amount of peroxidase is determined. It includes predominantly assays wherein horseradish peroxidase is conjugated to a ligand in order to label it and a luminescent reaction is used to detect or quantitate the label. This category includes ELISAs, competitive EIAs and nucleic acid hybridization assays, based on peroxidase labels. However, assays for measurement of free peroxidase, e.g. for analytical purposes, are also included.

A review of luminescent assays has been published by L. J. Kricka, Clinical Chemistry 37, 1472–1481 (1991).

The sensitivity of the peroxidase-catalysed chemiluminescent oxidation of DPDs can be enhanced by including in the reagents an enhancer, namely a 6-hydroxybenzothiazole (European Patent No. 87959B), a phenol selected from a narrowly defined class (European Patent No. 116454B or U.S. Pat. No. 4,598,044), or an aromatic amine selected from a narrowly defined class (U.K. Patent No. 2162946B or U.S. Pat. No. 4,729,950). A further class of substituted phenols that enhance chemiluminescent reactions of this type are phenols substituted in ortho and/or para positions by imidazolyl or benzimidazolyl (U.K. Patent No. 2205945B, European Patent No. 296752B). These patents are owned by National Research Development Corporation. European Patent Application Publication No. 219352A (Minnesota Mining and Mfg. Co.) describes various aromatic amines, including some of those previously mentioned in U.K. Application 2162946A, as enhancers. It is an object of the Invention to extend the range of effective enhancers. This is a difficult task because no theory or mechanism has been published to explain how one should attempt to select candidate compounds to try as enhancers. For the purposes of the present application the term "enhancer" and related terms will be used to include compounds that increase the total light output and/or the signal:background ratio of a chemiluminescent assay, at at least one concentration of compound.

SUMMARY OF THE INVENTION

It has now been found that certain organoboron compounds are effective enhancers of chemiluminescence in a reaction between a dihydrophthalaztnedione (DPD), a peroxidase enzyme catalyst and an oxidant. The enhancers of the present Invention include compounds of formula (I)

in which R, W, X, Y and Z have the following meanings;

R is selected from hydrogen, n-butyl, O,O-propylene (a cyclic ether), 4'-chlorophenyl and 3',5'-dichlorophenyl, W is selected from hydrogen, hydroxy, methyl, methoxy and chloro, X Is selected from hydrogen, methyl, chloro, amino and nitro, Y is selected from hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl, Z is selected from hydrogen, 5-chloro, 5-bromo, 5-(3'-trifluoromethyl) phenylazo, or 6-chloro, W and X together may represent a fused benzene ring and X and Y together may represent a fused benzene ring substituted by hydroxy in the 6 position of the naphthalene ring numbering, provided that when R is hydrogen, W, X, Y, Z are each separately hydrogen;

when R, W, X and Z are each hydrogen Y is selected from iodo, bromo, chloro, trimethylsilyl, phenoxy, phenyl, 4'-chloroanilino, methyl, 4'-boronylphenyl, 2'-carboxyethenyl;

when Y is hydrogen and the Rs together represent O,O-propylene (a cyclic ether), X is hydrogen;

when R, N and Z are each hydrogen, X and Y together represent a fused benzene ring substituted by hydroxy in the 6-position of the naphthalene ring numbering;

when W, X and Z are each hydrogen, R is n-butyl and Y is bromo or 4'-bromophenyl;

when W, X and Z are each hydrogen, R is 4'-chlorophenyl and Y is chloro;

when W and Y are each hydrogen, R is 3',5'-dichlorophenyl, X is chloro and Z is 5-chloro;

when W is methoxy, Z is 5-bromo;

when W is hydroxy, Z Is 5-(3'-trifluoromethyl)phenylazo;

when W is chloro, X is chloro;

when Y is chloro, X is nitro or chloro;

when Y is carboxy, X Is nitro;

when W and Y are each chloro and X is amino, Z is 6-chloro;

and the compounds bis(catechol)borate, boroglycine, pentaerythritol borate, 4-(3'-borono-4'-hydroxyphenylazo) benzoic acid, diphenylisobutoxyborane, diphenylboronic anhydride, dimethylphenylboronic acid (substitution pattern not established).

Of the compounds listed above those with O-alkyl groups may undergo spontaneous hydrolysis, e.g. diphenylisobutoxyborane, 4-(4'-bromophenyl)phenyl-di-n-butoxyborane or 4-bromophenyl-di-n-butoxyborane. Others containing the structure $(Aryl\text{-}O)_2\text{-}B\text{-}Aryl$ may also undergo spontaneous hydrolysis, e.g. di(3',5'-di-chlorophenoxy)-3,5- dichlorophenylborane or 4-chlorophenyl-di-(4'-chlorophenoxy)borane.

The enhancers of the present invention that fall into formula (I) may be easily looked at by means of the table below in which H is hydrogen and the key to the compound reference numbers is present in the Examples (compounds 5001, 5003, 5004, 5006 and 5007 as illustrated by FIGS. 1–5, respectively)

TABLE

| | R | W | X | Y | Z |
|---|---|---|---|---|---|
| 5001 | H | H | H | bromo | H |
| 5003 | H | H | amino | H | H |
| 5004 | H | H | H | H | H |
| 5006 | H | H | H | iodo | H |
| 5007 | H | H | H | 2'-carboxyethenyl | H |
| 1001 | H | H | H | trimethylsilyl | H |
| 1003 | H | methoxy | H | H | 5-bromo |
| 1005 | H | hydroxy | H | H | 5-(3'-trifluoro methyl)phenylazo |
| 1009 | H | methyl | H | H | H |
| 1010 | H | H | H | phenoxy | H |
| 1011 | H | H | H | phenyl | H |
| 1012 | 0,0-propylene | H | H | H | H |
| 1013 | 1015, 1017, 1018, 1019, 1036 and 1048 named compounds | | | | |
| 1021 | H | H | nitro | chloro | H |
| 1022 | H | chloro | chloro | H | H |
| 1024 | H | H | chloro | chloro | H |
| 1026 | H | chloro | amino | chloro | 6-chloro |
| 1028 | H | H | chloro | H | H |
| 1029 | H | H | H | chloro | H |
| 1030 | H | H | nitro | H | H |
| 1033 | H | H | H | 4'-chloroanilino | H |
| 1034 | H | H | H | methyl | H |
| 1037 | H | H | H | 4'-boronyl-phenyl | H |
| 1038 | n-butyl | H | H | 4'-bromo phenyl | H |
| 1040 | 3',5'-dichloro-phenyl | H | chloro | H | 5-chloro |
| 1041 | 4'-chloro-phenyl | H | H | chloro | H |
| 1044 | n-butyl | H | H | bromo | H |
| 1045 | H | H | nitro | carboxy | H |
| 1006 | fused benzene, hydroxy substituted in 6 position of naphthalene ring | | | | |
| 1002 | fused benzene | | | | |

While the invention applies to increasing the light output and/or the signal:background ratio from any chemiluminescent reaction involving the above-stated reaction partners, for any purpose, it is primarily of interest in connection with an assay. The term "assay" herein covers detection, semi-quantitation and quantitation. Typically, the assay is carried out so that the light output is relatable to the amount of peroxidase employed, the peroxidase then being the substance directly determined. The ratio of light output when peroxidase is present in the sample to light output when it is absent becomes important in assuring the sensitivity of the assay. This is conveniently termed a "signal to background" ratio. Similarly, if the substance to be determined is another of the reaction partners, the "signal" denotes the presence of the substance to be determined, the "background" its absence.

Although the invention is usable to determine the presence or amount of any one of the four above-stated reaction partners, such a reaction partner is not necessarily itself the substance to be assayed. Thus, the oxidant can be produced as a result of an earlier reaction or cascade of earlier reactions carried out on a sample. The peroxidase or the luminol can be in the form of a conjugate to, say, an antibody which is used in an immunoassay to determine an antigen. The invention is accordingly applicable to any method of diagnostic assay of a substance, the presence or amount of which is relatable to the presence or amount of a reaction partner selected from the group consisting of a DPD, a peroxidase enzyme, an oxidant and an enhancer which together are reactable in a chemiluminescent reaction and wherein the reaction is carried out, the light output is detected or measured and thence the presence or amount of the substance to be assayed is related to the light output.

The invention also includes a kit for use in the assay comprising the DPD, the peroxidase and the enhancer. The oxidant could be supplied separately or included in the kit.

DESCRIPTION OF THE PREFERRED EMBODIMENTS

The enhancers of the present invention include 4-iodophenylboronic acid (PIBA), 4-bromophenylboronic acid (PBBA), 4-chlorophenylboronic acid, 3-chlorophenylboronic acid, 3,4-dichlorophenylboronic acid, 2,3-dichlorophenylboronic acid, 5-bromo-2-methoxybenzeneboronic acid, 3-nitrophenylboronic acid, 4-chloro-3-nitrophenylboronic acid, 3-aminophenylboronic acid, 3-amino-2,4,6-trichlorophenylboronic acid, 4-(2'-carboxyethenyl)phenylboronic acid, 1-naphthaleneboronic acid, 6-hydroxy-2-naphthaleneboronic acid, phenylboronic acid, 2-methylphenylboronic acid, 4-methylphenylboronic acid, dimethyl-phenylboronic acid, 4-bromophenyl-di-n-butoxyborane, 4-carboxy-3-nitrophenylboronic acid, 4-(trimethylsilyl)benzeneboronic acid, 4-biphenylboronic acid, 4-(phenoxy)benzeneboronic acid, 4-(3'-borono-4'-hydroxyphenylazo)benzoic acid, diphenylisobutoxyborane, 4-(4'-chloroanilino)phenylboronic acid, 4,4'-bis (phenylboronic acid), 4-(4'-bromophenyl)phenyl-di-n-butoxyborane, di(3',5'-dichlorophenoxy)-3,5-dichlorophenylborane, 4-chlorophenyl-di-(4'-chlorophenoxy)borane, pentaerythritol borate, boroglycine, 2-phenyl-1,3,2-dioxaborinane, bis(catechol)borate and 2-hydroxy-5-[(3'-trifluoromethyl)phenylazo]benzeboronic acid and diphenylboronic anhydride.

The preferred enhancers are PIBA, PBBA, 4-biphenylboronic acid, 4-(trimethylsilyl)-benzeneboronic acid, boroglycine, 2-hydroxy-5-[(3'-(trifluoromethyl) phenylazo]benzeneboronic acid, 4-chloro-3-nitrophenylboronic acid, 4-chlorophenylboronic acid, 4-(2'-carboxyethenyl)phenylboronic acid, 4-(4'-bromophenyl) phenyl-di-n-butoxyborane, 4-chlorophenyl-di-(4'-chlorophenoxy)borane, 4,4'-bis(phenylboronic acid), diphenylboronic anhydride, 4'-chloro anilino)phenylboronic acid and 4-bromophenyl-di-n-butoxyborane as they increase light output as well as reducing the background luminescene. The remaining enhancers exert their effect primarily by reducing the background luminescence, and thereby improving the signal:background ratio.

BRIEF DESCRIPTION OF THE DRAWINGS

The invention is now further described with reference to the accompanying drawing in which.

The improvement in signal;background ratio is of importance in controlling the sensitivity of chemiluminescent assays. The enhancers of the present invention are therefore of particular use in those situations where a high degree of sensitivty is required, for example in blotting assays. Thus the present invention is of especial use in blotting assays including Western, Southern and Northern blotting assays, as well as dot blots and other nucleic acid hybridisation assays.

The best results are obtained at higher pH. Preferably the pH is in the range 7.5 to 9 at the time of mixing all the reagents.

Any chemiluminescent DPD can be used in the invention, that is to say any DPD which is oxidisable in the presence of a peroxidase catalyst by an added oxidant to give chemiluminescence can be used. Examples are luminol, isoluminol, ABEI and AHEI, and 7-dimethylaminonaphthalene-1,2-dicarboxylic acid hydrazide, of which luminol is normally preferred. The DPD can be free or conjugated to a ligand to provide a direct label. Such luminophore-labelled assays are known in the art.

The oxidant can be any added substance (not oxygen itself) which oxidises the DPD in a light-emitting reaction; hydrogen peroxide is usual, but a perborate, such as the sodium salt, is an alternative.

The peroxidase enzyme will normally be HRP and of a grade appropriate to use in luminescent assays. Preferably the HRP is a basic isoenzyme, for example of Sigma Type VIA or IX. It can be free or conjugated to a ligand.

The concentrations of the reaction partners of the chemiluminescent reaction will depend on the nature of the assay being carried out and particularly on which of them is being assayed. Generally stated, the light output is greater, the greater the concentration of DPD. Thus, when peroxidase or oxidant is being assayed, the use of excess DPD is recommended. Generally stated, the DPD concentration is desirably from 0.5 micromole to 200 millimoles per liter, preferably 0.5 to 100 micromoles/liter. Generally stated, the oxidant concentration is desirably in the range 0.5 micromoles to 300 millimoles/liter, preferably 10 to 200 millimoles/liter.

The concentration of peroxidase is of interest if peroxidase is not the reaction partner being assayed. Excess peroxidase does not normally have a marked effect on light intensity, the peroxidase being a catalyst which is recycled. Where luminol or the oxidant is being assayed, therefore, the perozidase need only be present in a modest concentration, such as 0.01 microgram to 5000 mg./liter, preferably not more than 50 mg./liter, but depending on the actitvity of the peroxidase per gram.

The concentration of the enhancer will usually be in the range 0.01 micromole to 4 moles/liter, preferably 10 micromoles to 100 millimoles/liter. It is believed that the enhancer or a species or derivative thereof competes with the DPD in the reaction and it is therefore desirable to use a considerable excess of DPD relative to the enhancer, preferably between 2 and 20 times the molar concentration of the enhancer.

In brief, all conditions and features of the chemiluminescent reactions, the reaction partners thereof, applications of the assay and so on (except where inconsistent with the above description) can be as set forth in European Patent No. 116454B, the disclosure of which in relation thereto is herein incorporated by reference.

The following Examples illustrate the invention. In the Examples, compounds of series 5000 are obtainable from the stated sources, compounds of series 1000 are identified by means of their Chemical Abstracts Registry Number and others are obtainable from US Borax Research Corporation, 412 Crescent Nay, Anaheim, Calif. 92901-9794.

EXAMPLE 1

This Example shows that para-bromophenylboronic acid (PBBA) enhances a chemiluminescent reaction between luminol (LU) horseradish peroxidase (HRP), and $H_2O_2$ giving a high signal: background ratio.

1. Effect of PBBA (Compound 5001) on the signal:background ratio of a chemiluminescent reaction PBBA was added in various concentrations (range 0.051 μg to 0.5 μg) to a luminol-$H_2O_2$ in the presence and absence of HRP. The luminol-hyddrogen peroxide reagent was prepared as follows: sodium luminol (12.5 mg) was dissolved in 50 ml of Tris buffer (0.1 mol/l, pH 8.6), and 15.5 μl of hydrogen peroxide (30% w/v) was mixed with 0.5 ml of Tris buffer (0.1 mol/l, pH 8.6). These two solutions were combined and protected from light. The luminol-hydrogen peroxide reagent (100 μl of a 1:10 dilution) was added to a cuvette together with. either 10 μl of HRP Type VI A (HRP, Sigma Chemical Co., 1:50,000 dilution) or as a control 10 μl of Tris Buffer (0.1 mol/l, pH 8.6), and various amounts of PBBA (Aldrich Chemical Co.), range 0.05 μg–0.5 μg in 0.1 mol/l Tris, pH 8.6). The reagents were mixed and the light emission recorded after 5 minutes on a Berthold Biolumat LB9500C.

This experiment was repeated, replacing the luminol with isoluminol. The measured light output and signal:background ratios are shown in Table 1. Column (a) shows that PBBA enhances the light emission in the luminol-HRP-peroxidase reaction. Column (b) shows that addition of PBBA reduces the background level of luminescence. Columns (d) and (e) show a similar effect with isoluminol.

TABLE 1

| | Luminol | | | Isoluminol | | |
|---|---|---|---|---|---|---|
| PBBA (μg) | (a) Signal (with HRP) | (b) Signal (no HRP) | (c) Signal: Background ratio | (d) Signal (with HRP) | (e) Signal (no HRP) | (f) Signal: Background ratio |
| 0 | 87,616 | 18,833 | 4.7 | 14,485 | 7927 | 1.8 |
| 0.05 | 101,227 | 16,556 | 6.1 | 15,772 | 7664 | 2.1 |
| 0.1 | 108,213 | 16,065 | 6.7 | 16,553 | 6114 | 2.7 |
| 0.2 | 112,644 | 13,890 | 8.1 | 68,282 | 5736 | 11.9 |
| 0.3 | 122,116 | 10,899 | 11.2 | 619,880 | 5613 | 110.4 |
| 0.4 | 133,401 | 10,706 | 12.5 | 775,965 | 5278 | 147.0 |
| 0.5 | 151,572 | 8,963 | 16.9 | | | |

2. Effect of PBBA on the light output of a chemiluminescent reaction

The above experiment was repeated this time keeping the amount of PBBA enhancer fixed and varying the amount of HRP. The reagents used were 100 μl of luminol-hydrogen peroxide, either (a) 40 μl of PBBA (0.01 mg/ml in 0.1 mol/l Tris buffer, pH 8.6) or (b) as a control, 40 μl of Tris buffer (0.1 mol/l pH 8.6) and various amounts of HRP (range 5 μl to 40 μl of 1:50,000 dilution of a 1 mg/ml stock solution).

The reagents were mixed and light output recorded after 5 minutes on a Berthold Btolumat LB9500C. The measured signal (light output) and signal:background ratios are shown in Table 2. By comparing columns (a) and (b) it can be seen that PBBA increased the light output of the chemiluminescent reaction at all concentrations tested. An improved signal:background ratio is shown by comparing results with HRP present with the zero HRP results.

TABLE 2

| HRP (μg) | (a) Signal (with PBBA) | Signal: Background Ratio | (b) Signal (no PBBA) | Signal: Background Ratio |
|---|---|---|---|---|
| 0 | 9,125 | | 13,405 | |
| 100 | 15,861 | 1.7 | 15,148 | 1.1 |
| 200 | 22,895 | 2.5 | 19,384 | 1.4 |
| 400 | 38,495 | 4.2 | 25,968 | 1.9 |
| 600 | 61,491 | 6.7 | 33,964 | 2.5 |
| 800 | 105,972 | 11.6 | 34,790 | 2.6 |

EXAMPLE 2

Effect of organoboron compounds on a chemiluminescent reaction

A solution of 2,4-dichlorophenylboronic acid (5002) (1 mg/ml, Lancaster Synthesis Inc., Hindham, N.H.) was prepared as follows: 5 mg 2,4-dichlorophenylboronic acid was dissolved in 50 μl of DMSO, then added to 4950 μl of Tris buffer (0.1 mol/l, pH 8.6). Solutions of 3-aminophenylboronic acid (5003) (1 mg/ml, Sigma), 3-nitro-phenylboronic acid (5004) (1 mg/ml, Aldrich). phenylboronic acid (5004) (1 mg/ml, Aldrich) and butaneborinic acid (5005) (1 mg/ml, Sigma) were prepared in Tris buffer (0.1 mol/l, pH 8.6). The stock solution of HRP Type VIA (1 mg/ml) and luminol-hydrogen peroxide reagent were prepared as described previously. Luminol-hydrogen peroxide (100 μl, 1:10 dilution) was mixed with either 10 μl of HRP (1:50,000 dilution) or, 10 μl of Tris buffer (0.1 mol/l, pH 8.6). The light emission was measured in a Berthold Biolumat LB9500C, and then 5 μl of 2,4-dichlorophenylboronic acid was added and the light emission was remeasured. A control without any test compound was run in parallel.

The above experiment was repeated except that 2,4-dichlorophenylboronic acid was replaced by 3-aminophenylboronic acid (5 μl), 3-nitrophenylboronic acid (5 μl), phenylboronic acid (5 μl), or butaneborinic acid (40 μl).

The measured light output and signal:background ratios are shown in Table 3 for each compound tested and its control. The control consisted of buffer in place of the compound under test as an enhancer. None of the compounds tested increased the light emisston from the HRP catalyzed oxidation of luminol. However, the signal to background ratio was improved in the case of 3-nitrophenylboronic acid, phenylboronic acid, and 3-aminophenylboronic acid as compared to their control values. This was due to the reduction in the background light emission from the luminol-peroxide reagent caused by these compounds. Thus, these three compounds are of use in the present invention. 2,4-dichlorophenylboronic acid and butaneboronic acid are not of use as they neither increased the light output or the signal: background ratio. The small increase in light output observed for butaneborinic acid is not significantly relevant to be of use in the present invention.

TABLE 3

| | | Signal (with HRP | Signal (no HRP | Signal: Background Ratio |
|---|---|---|---|---|
| 2,4-dichlorophenyl- | control | 271,566 | 20,990 | 12.9 |
| boronic acid (5002) | test | 128,274 | 16,246 | 7.9 |
| 3-nitrophenyl- | control | 175,440 | 25,196 | 6.9 |
| boronic acid | test | 132,887 | 16,400 | 8.1 |
| phenylboronic acid | control | 156,658 | 26,564 | 5.9 |
| (5004) | test | 54,554 | 5,601 | 9.7 |
| 3-aminophenyl- | control | 249,204 | 19,615 | 12.7 |
| boronic acid (5003) | test | 60,222 | 1,038 | 58.0 |
| butaneborinic acid | control | 64,652 | 39,640 | 1.6 |
| (5005) | test | 65,197 | 54,389 | 1.2 |

EXAMPLE 3

Screening of further organoboron compounds

Figures 1, 2, 3, 4, 5, 6, 7, 8, 9, 10, 11, 12, 13, 14:
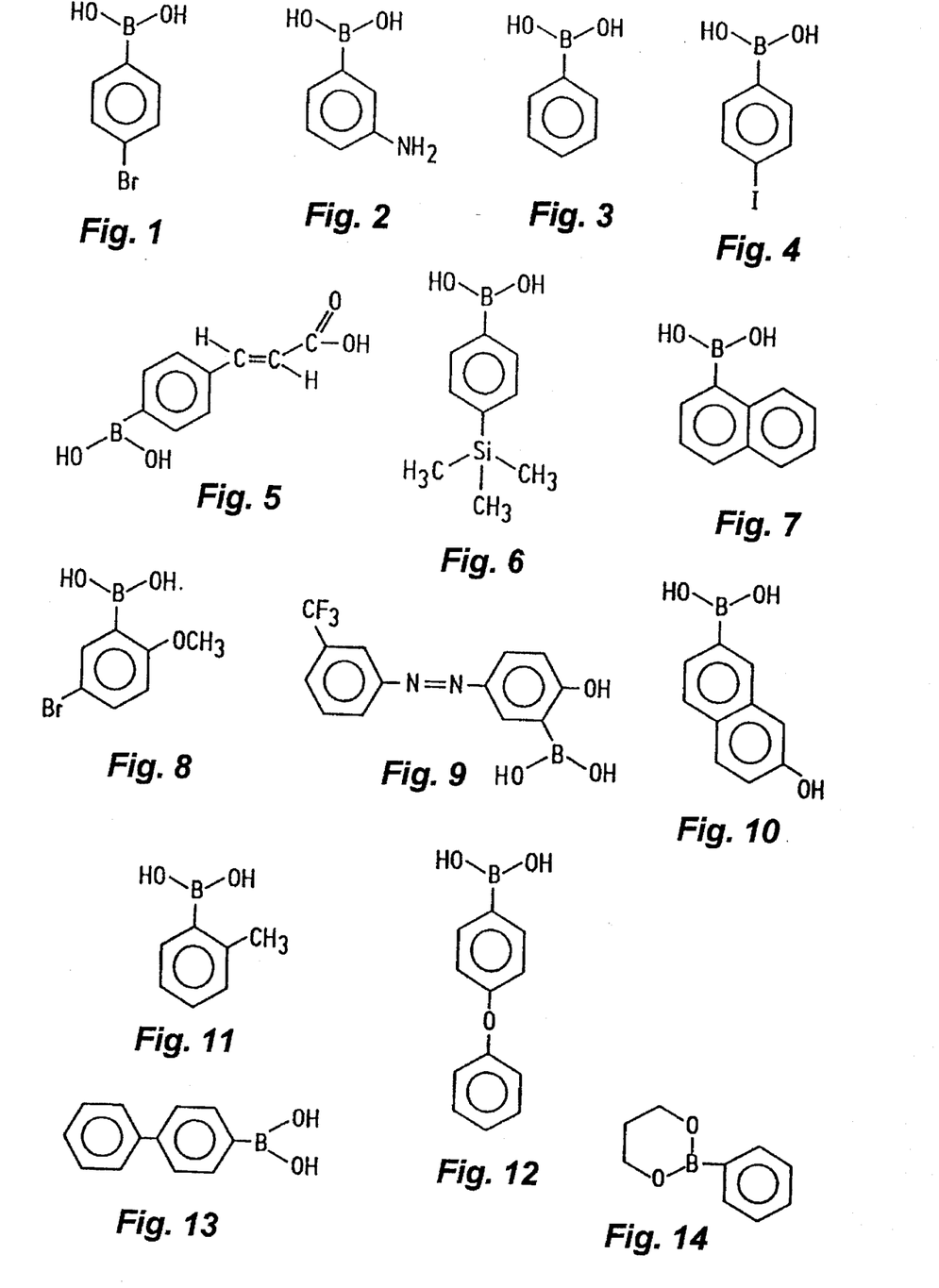
FIGS. 1–35 show structures of compounds of the invention.

The stock solutions of HRP Type VIA (1 mg/ml) and luminolhydrogen peroxide were prepared as described above. 10 μl test compound of varying concentration (0.01–1 mg/ml) was added to luminol-hydrogen peroxide (100 μl, 1:10 dilution). 10 μl HRP Type VIA or as a control 10 μl Tris buffer was added. The light emission was measured on a Berthold Biolumat LB9500C The following test compounds were all screened in this manner. Chemical Abstracts Registry Numbers are in brackets:

1001 4-(trimethylsilyl) benzeneboronic acid (17865-11-1) FIG. 6
1002 1-naphthaleneboronic acid (31093-44-4) FIG. 7
1003 5-bromo-2-methoxybenzeneboronic acid (84694-45-1) FIG. 8
1004 2-biphenylboronic acid (4688-76-0) FIG. 9
1005 2-hydroxy-5-[(3'-(trifluoromethyl)phenylazo]benzene boronic acid
1006 6-hydroxy-2-naphthaleneboronic acid FIG. 10

Figure 15:
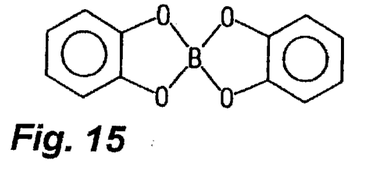
Figure 16:
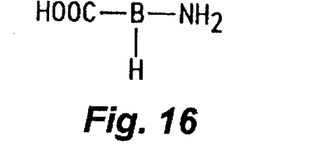
Figure 17:
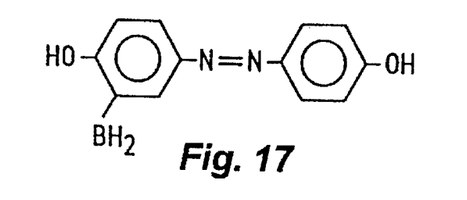
Figure 18:
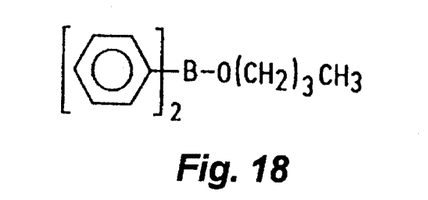
Figure 19:
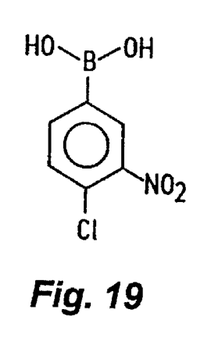
Figure 20:
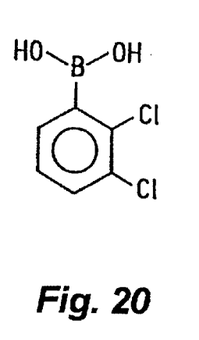
Figure 21:
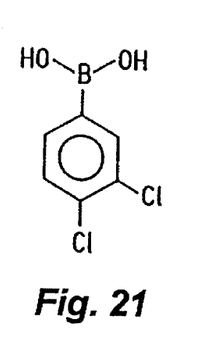
Figure 22:
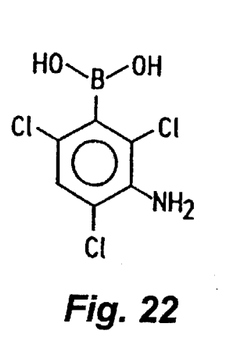
Figure 23:
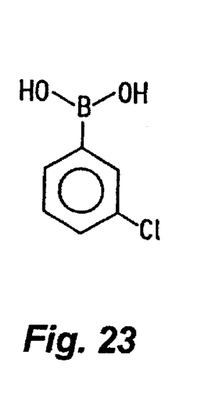
Figure 24:
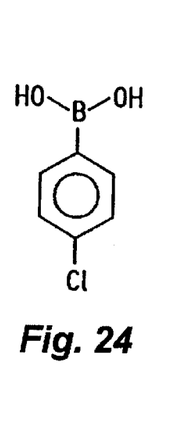
Figure 25:
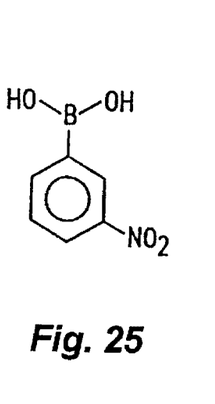
Figure 26:
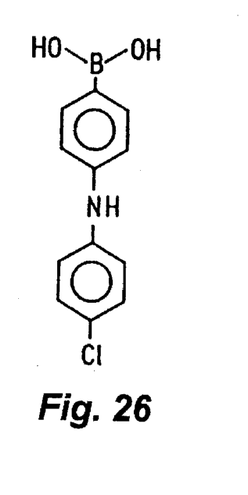
Figure 27:
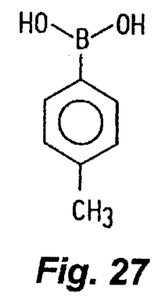
Figure 28:
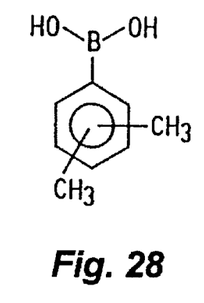
Figure 29:
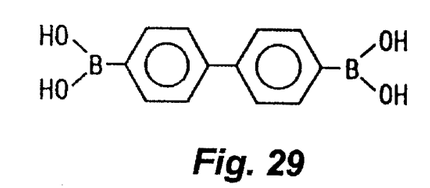
Figure 30:
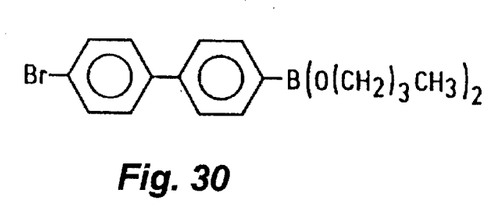
Figure 31:
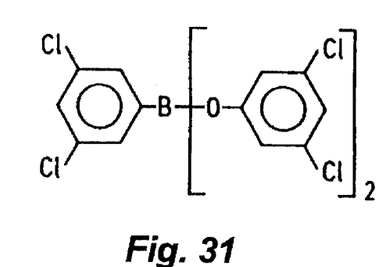
Figure 32:
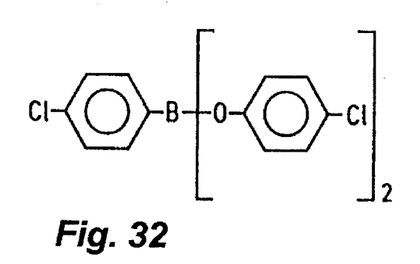
Figure 33:
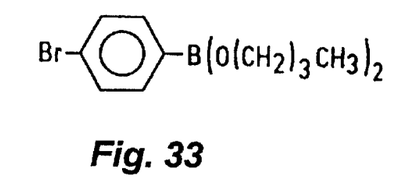
Figure 34:
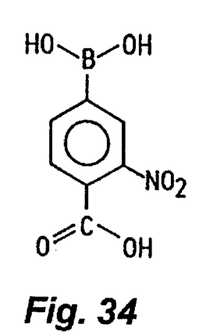
Figure 35:
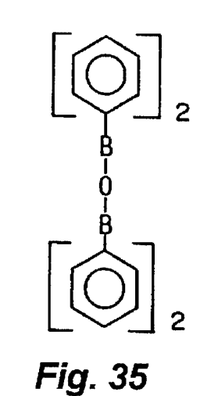

-continued 1007 1-thianthreneboronic acid (108847-76-3)
1008 4-dibenzofuranboronic acid (100124-06-9)
1009 2-tolueneboronic acid (16419-60-6) FIG. 11
1010 4-(phenoxy)benzeneboronic acid (109412-50-2) FIG. 12
1011 4-biphenylboronic acid (5122-94-1) FIG. 13
1012 2-phenyl-1,3,2-dioxaborinane (4406-77-3) FIG. 14
1013 bis(catechol)borate FIG. 15
1014 boraxarophenanthrene
1015 boroglycine FIG. 16
1016 tetraphenylboron sodium (143-66-8)
1017 pentaerythritol borate
1018 4-(3'-borono-4'-hydroxyphenylazo)benzoic acid FIG. 17
1019 diphenylisobutoxyborane (23147-97-9) FIG. 18
1020 2,4,6-trichlorophenylboronic acid (73852-18-3)
1021 4-chloro-3-nitrophenylboronic acid FIG. 19
1022 2,3-dichlorophenylboronic acid FIG. 20
1023 2,5-dichlorophenylboronic acid (135145-90-3)
1024 3,4-dichlorophenylboronic acid FIG. 21
1025 3,5-dichlorophenylboronic acid (67492-50-6)
1026 3-amino-2,4,6-trichlorophenylboronic acid FIG. 22
1027 2-chlorophenylboronic acid
1028 3-chlorophenylboronic acid (63503-60-6) FIG. 23
1029 4-chlorophenylboronic acid (1679-18-1) FIG. 24
1030 3-nitrophenylboronic acid (13331-27-6) FIG. 25
1031 3-chloroacetylaminophenylboronic acid
1032 3-(2'-methylbutylamino)phenylboronic acid
1033 4-(4'-chloroanilino)phenylboronic acid FIG. 26
1034 4-methylphenylboronic acid (5720-05-8) FIG. 27
1035 1,4-phenyldiboronic acid
1036 dimethylphenylboronic acid (position of methyl groups not established) FIG. 28
1037 4,4'-bis(phenylboronic acid) (4151-80-8) FIG. 29
1038 4-(4'-bromophenyl)phenyl-di-n-butoxyborane FIG. 30
1039 di-(3',4',6'-trichlorophenoxy)-3,4,6-trichlorophenyl-borane
1040 di-(3',5'-dichlorophenoxy)-3,5-dichlorophenylboran FIG. 31
1041 4-chlorophenyl-di-(4'-chlorophenoxy)borane FIG. 32
1042 3-nitrophenylboronic acid, sodium salt
1043 3-nitrophenylboronic acid, calcium salt
1044 4-bromophenyl-di-n-butoxyborane FIG.33
1045 4-carboxy-3-nitrophenylboronic acid FIG. 34
1046 2-benzimidazolylphenylboronic acid (58534-74-0)
1047 di-(1-naphthoxy)-1-naphthylborane
1048 diphenylboronic anhydride FIG. 35
1049 2-boromethylphenyl-di-(2'-boromethylphenoxy)borane
1050 2-(methylthiomethyl)phenylboronic acid
1051 methyl-(2-tolylboronic acid)sulfoxide In Table 4, column (a) shows whether the test compound lowered the light output from the luminol-hydrogen peroxide solution (Y=yes, N=no). Column (b) shows whether the signal obtained after adding the HRP was greater in the presence of the test compound than in its absence, (Y=yes, N=no). A compound showing Y in column (b) is of preferred use in the present invention as it increases the light output of the reaction. Column (c) shows whether there was an increase in the signal:background ratio by over 25% of the control value (Y=yes, N=no), column (d) shows the actual calculated value of the signal:background ratio (value of column (b)/value of column (a)). Column (c) is a simplified representation of the results in column (d). Signal:background ratio is the ratio of light output in the presence and absence of HRP with the test compound being present.

All compounds increasing the signal:background ratio by over 25% at least one concentration (Y in column (c)) are of use in the present invention. Those compounds that increase the light output (Y in column (b)) as well as increasing the signal:background ratio (Y in column (c)) are of especial use in the present invention. Thus, compounds 1001, 1002, 1003, 1005, 1006, 1009, 1010, 1011, 1012, 1013, 1015, 1017, 1018, 1019, 1021, 1022, 1024, 1026, 1028, 1029, 1030, 1033, 1034, 1036, 1037, 1038, 1040, 1041, 1044, 1045 and 1048 are of use in increasing the signal:background ratio of a chemiluminescent reaction. Of these, compounds 1001, 1005, 1011, 1015, 1021, 1029, 1033, 1037, 1038, 1041, 1044 and 1048 also increase the light output and are therefore of especial use in the present invention.

TABLE 4

| Compound | mg/ml | (a) Decrease in background (without HRP with test cpd.) | (b) Increase in signal (with HRP, with test cpd.) | (c) Increase in signal: background ratio | (d) Signal: Background: ratio (control = with no enhancer) |
|---|---|---|---|---|---|
| 1001 | 1 | Y | N | Y | 10.9 (2.1) |
|  | 0.1 | Y | Y | Y | 6.7 |
|  | 0.01 | Y | Y | Y | 3.2 |
| 1002 | 1 | Y | N | N | 0.7 (2.3) |
|  | 0.1 | Y | N | Y | 3.4 |
|  | 0.01 | Y | N | N | 2.5 |
| 1003 | 1 | Y | N | N | 2.6 (2.3) |
|  | 0.1 | Y | N | Y | 12.1 |
|  | 0.01 | Y | N | Y | 8.6 |
| 1004 | 1 | Y | N | N | 1.7 (2.3) |
|  | 0.1 | Y | N | N | 2.2 |
|  | 0.01 | Y | N | N | 1.9 |
| 1005 | 1 | Y | N | N | 2.4 (2.1) |
|  | 0.1 | N | Y | Y | 2.9 |
|  | 0.01 | N | Y | Y | 2.7 |
| 1006 | 1 | Y | N | N | 0.3 (1.8) |
|  | 0.1 | Y | N | N | 1.5 |
|  | 0.01 | Y | N | Y | 5.8 |
| 1007 | 1 | Y | N | N | 1.8 (2.1) |
|  | 0.1 | Y | N | N | 2.5 |
|  | 0.01 | Y | N | N | 2.1 |
| 1008 | 1 | Y | N | N | 1.3 (2.5) |
|  | 0.1 | Y | N | N | 1.5 |
|  | 0.01 | Y | N | N | 1.6 |
| 1009 | 1 | Y | N | N | 0.6 (1.8) |
|  | 0.1 | Y | N | Y | 2.5 |
|  | 0.01 | Y | N | N | 1.9 |
| 1010 | 1 | Y | N | Y | 5.0 (2.5) |
|  | 0.1 | Y | N | Y | 4.6 |
|  | 0.01 | Y | N | N | 3.0 |
| 1011 | 1 | Y | Y | Y | 48.7 (2.5) |
|  | 0.1 | Y | Y | Y | >125 |
|  | 0.01 | Y | Y | Y | >125 |
| 1012 | 1 | Y | N | Y | 17.1 (2.5) |
|  | 0.1 | N | N | N | 2.2 |
|  | 0.01 | N | Y | N | 2.2 |
| 1013 | 1 | Y | N | N | 1.2 (1.8) |
|  | 0.1 | Y | N | Y | 3.1 |
|  | 0.01 | Y | N | Y | 12.6 |
| 1014 | 1 | Y | N | N | 1.8 (2.5) |
|  | 0.1 | Y | N | N | 1.6 |
|  | 0.01 | Y | N | N | 2.3 |
| 1015 | 1 | Y | N | Y | 3.1 (2.1) |
|  | 0.1 | Y | Y | Y | 2.9 |
|  | 0.01 | Y | Y | N | 2.3 |
| 1016 | 1 | Y | N | N | 2.3 (1.9) |
|  | 0.1 | Y | N | N | 2.0 |
|  | 0.01 | Y | N | N | 2.0 |
| 1017 | 1 | Y | N | N | 1.8 (1.8) |
|  | 0.1 | Y | Y | Y | 2.5 |
|  | 0.01 | Y | N | N | 1.8 |
| 1018 | 1 | Y | N | Y | 4.2 (1.9) |
|  | 0.1 | Y | N | Y | 24.5 |
|  | 0.01 | Y | N | Y | 5.0 |
| 1019 | 1 | Y | N | N |  |
|  | 0.1 | Y | N | N | 3.0 (2.9) |
|  | 0.01 | Y | N | Y | 3.2 (2.0) |
| 1020 | 1 | Y | N | N |  |
|  | 0.1 | Y | N | N |  |
|  | 0.01 | Y | N | N | 2.2 (2.0) |
| 1021 | 1 | Y | Y | Y | 247.9 (4.5) |
|  | 0.1 | Y | Y | Y | 44.5 (2.8) |
|  | 0.01 | Y | Y | Y | 2.3 (1.8) |
| 1022 | 1 | Y | N | N |  |
|  | 0.1 | Y | N | Y | 3.6 (2.7) |
|  | 0.01 | Y | N | N | 2.2 (2.0) |

TABLE 4-continued

| Compound | mg/ml | (a) Decrease in background (without HRP with test cpd.) | (b) Increase in signal (with HRP, with test cpd.) | (c) Increase in signal: background ratio | (d) Signal: Background: ratio (control = with no enhancer) |
|---|---|---|---|---|---|
| 1023 | 1 | Y | N | N | |
| | 0.1 | Y | N | N | 3.1 (2.7) |
| | 0.01 | Y | N | N | |
| 1024 | 1 | Y | N | Y | 7.6 (4.5) |
| | 0.1 | Y | Y | Y | 5.4 (2.8) |
| | 0.01 | Y | N | N | |
| 1025 | 1 | Y | N | N | |
| | 0.1 | Y | N | N | |
| | 0.01 | Y | N | N | 2.1 (2.0) |
| 1026 | 1 | Y | N | Y | 40.5 (4.5) |
| | 0.1 | Y | Y | Y | 72.4 (2.8) |
| | 0.01 | Y | N | N | 2.1 (2.0) |
| 1027 | 1 | Y | N | N | |
| | 0.1 | Y | N | N | 3.2 (2.9) |
| | 0.01 | Y | N | N | 2.1 (2.0) |
| 1028 | 1 | Y | N | Y | 20.0 (4.5) |
| | 0.1 | Y | Y | Y | 4.2 (2.9) |
| | 0.01 | Y | N | N | |
| 1029 | 1 | Y | Y | Y | 1242.4 (4.5) |
| | 0.1 | Y | Y | Y | 315.0 (2.8) |
| | 0.01 | Y | Y | Y | 6.0 (1.8) |
| 1030 | 1 | Y | N | Y | 50.0 (4.5) |
| | 0.1 | Y | Y | Y | 12.5 (2.8) |
| | 0.01 | Y | N | N | |
| 1031 | 1 | Y | N | N | |
| | 0.1 | Y | N | N | 3.3 (2.9) |
| | 0.01 | Y | N | N | 2.1 (2.0) |
| 1032 | 1 | Y | N | N | |
| | 0.1 | Y | N | N | 3.4 (2.9) |
| | 0.01 | Y | N | N | |
| 1033 | 1 | Y | Y | Y | 173.9 (4.5) |
| | 0.1 | Y | Y | Y | 67.7 (2.8) |
| | 0.01 | Y | Y | Y | 4.1 (1.8) |
| 1034 | 1 | Y | N | N | |
| | 0.1 | Y | Y | Y | 41.2 (2.9) |
| | 0.01 | Y | Y | Y | 3.6 (1.9) |
| 1035 | 1 | Y | N | N | |
| | 0.1 | Y | N | N | |
| | 0.01 | Y | N | N | 2.1 (2.0) |
| 1036 | 1 | Y | N | N | |
| | 0.1 | Y | N | Y | 7.6 (2.9) |
| | 0.01 | Y | N | Y | 2.6 (2.0) |
| 1037 | 1 | Y | N | N | |
| | 0.1 | Y | Y | Y | 503.3 (2.9) |
| | 0.01 | Y | Y | Y | 35.5 (1.9) |
| 1038 | 1 | Y | Y | Y | 903.8 (4.5) |
| | 0.1 | Y | Y | Y | 2118.5 (2.9) |
| | 0.01 | Y | Y | Y | 442.2 (1.8) |
| 1039 | 1 | Y | N | N | |
| | 0.1 | Y | N | N | 3.4 (2.9) |
| | 0.01 | Y | N | N | |
| 1040 | 1 | Y | N | Y | 4.7 (4.5) |
| | 0.1 | Y | N | Y | 3.9 (2.9) |
| | 0.01 | Y | N | N | |
| 1041 | 1 | Y | Y | Y | 2606.2 (4.5) |
| | 0.1 | Y | Y | Y | 360.2 (2.8) |
| | 0.01 | Y | Y | Y | 6.3 (1.9) |
| 1042 | 1 | Y | N | N | 5.2 (4.5) |
| | 0.1 | Y | N | N | 3.6 (2.9) |
| | 0.01 | Y | N | N | 2.3 (2.0) |
| 1043 | 1 | Y | N | N | |
| | 0.1 | Y | N | N | 3.4 (2.9) |
| | 0.01 | Y | N | N | |
| 1044 | 1 | Y | N | Y | 147.1 (4.5) |
| | 0.1 | Y | Y | Y | 623.1 (2.7) |
| | 0.01 | Y | Y | Y | 38.5 (1.9) |
| 1045 | 1 | Y | N | Y | 68.5 (4.5) |
| | 0.1 | Y | Y | Y | 18.1 (2.8) |
| | 0.01 | Y | N | N | 2.2 (2.0) |
| 1046 | 1 | Y | N | N | |
| | 0.1 | Y | N | N | |
| | 0.01 | Y | N | N | |
| 1047 | 1 | Y | N | N | |
| | 0.1 | Y | N | N | |
| | 0.01 | Y | N | N | |
| 1048 | 1 | Y | N | Y | 100.0 (4.5) |
| | 0.1 | Y | Y | Y | 139.0 (2.7) |
| | 0.01 | Y | Y | Y | 3.1 (1.8) |
| 1049 | 1 | Y | N | N | |
| | 0.1 | Y | N | N | 3.2 (2.9) |
| | 0.01 | Y | N | N | |
| 1050 | 1 | Y | N | N | |
| | 0.1 | Y | N | N | 3.3 (2.9) |
| | 0.01 | Y | N | N | |
| 1051 | 1 | Y | N | N | |
| | 0.1 | Y | N | N | |
| | 0.01 | Y | N | N | |

EXAMPLE 4

Effect of different peroxidase enzymes on the PBBA enhancement of a chemiluminescent reaction Stock solutions (1 mg/ml in 0.1 mol/l Tris buffer, pH 8.6) of horseradish peroxidase Type VII, Type VIII and *Arthromyces ramosus* peroxidase (Sigma) were prepared. The luminol-hydrogen peroxide reagent was prepared as described previously. Luminolhydrogen peroxide reagent (100 µl, 1:10 dilution), either 40 µl of PBBA (0.01 mg/ml in 0.1 mol/l Tris buffer, pH 8.6) or as a control, 40 µl of Tris buffer (0.1 mol/l, pH 8.6), and 10 µl of HRP Type VII (1:50,000 dilution, 2 ng) were added to a cuvette. The reagents were mixed and the light emission was recorded after 5 minutes using a Berthold Btolumat LB9500C.

The above experiment was repeated and the HRP Type VII was replaced by HRP Type VIII (2 ng) or *Arthromyces ramosus* peroxidase (20 pg). The measured light output and signal:background ratios are shown in Table 5. PBBA did not increase the level of light output with any of the peroxidases tested, but the signal to background ratio was improved in all cases due to the background reduction caused by PBBA.

TABLE 5

| | Signal Reagent with PBBA | Signal: Background | Signal Reagent no PBBA | Signal Background |
|---|---|---|---|---|
| Blank | 27,820 | | 58,759 | |
| HRP Type VII | 49,703 | 1.8 | 77,694 | 1.3 |
| HRP Type VIII | 156,204 | 5.6 | 280,472 | 4.8 |
| *Arthromyces rasmosus* | 58,208 | 2.1 | 84,071 | 1.4 |

EXAMPLE 5

Assay of peroxidase-antibody conjugate utilizing PBBA

Anti-mouse IgG (whole molecule) peroxidase conjugate (Sigma Chemical Co.) was diluted (1:5000) in 0.1 mol/l Tris buffer (pH 8.6). The luminol-hydrogen peroxide was prepared as described previously. The following reagents were added to a cuvette: 100 µl of luminol-hydrogen peroxide (1:10 dilution), either 40 µl of PBBA (0.01 mg/ml in 0.1 mol/l Tris buffer) or as a control, 40 µl of Tris buffer (0.1 mol/l, pH 8.6), and different amounts of anti-mouse IgG (5 µl, 10 µl, 20 µl, 30 µl, 40 µl). The reagents were mixed and the light emission was measured using a Berthold Biolumat LB9500C.

The results are shown in Table 6. In the presence of PBBA the light emission was increased and the signal to background ratio for the assay of the HRP conjugate was significantly improved.

TABLE 6

| Anti-mouse IgG-HRP (ml) | Signal with PBBA | Signal: Background | Signal no PBBA | Signal: Background |
|---|---|---|---|---|
| 0 | 18,832 | | 23,112 | |
| 5 | 27,665 | 1.5 | 17,858 | 0.8 |
| 10 | 32,849 | 1.7 | 27,458 | 1.2 |
| 20 | 68,994 | 3.7 | 29,850 | 1.3 |
| 30 | 407,087 | 21.6 | 32,417 | 1.4 |

EXAMPLE 6

Enhanced chemiluminescent anti-oxidant assay using PBBA

The luminol-peroxide reagent (100 µl), PBBA (40 µl, 1:100 dilution of 1 mg/ml) and HRP (10 µl, 1:50,000 dilution of 1 mg/ml stock) were mixed together and the light emission measured for 25 minutes. A sample of human serum (2 µl, 1:10 dilution in 0.1 mol/l Tris buffer, pH 8.6) was added and the light emission measured for a further 75 minutes.

Table 7 shows that addition of serum quenched the light emission and that after a 34 minute lag the light emission returns to its original level.

TABLE 7

| | Time (minutes) | Light units | Time (minutes) | Light units |
|---|---|---|---|---|
| | 0 | | 5 | 50 | 5 |
| | 10 | 16 | 60 | 15 |
| | 20 | 68 | 70 | 49 |
| (serum | 25 | 88 | 80 | 60 |
| added) | 26 | 3 | 90 | 81 |
| | 30 | 3 | 100 | 90 |

EXAMPLE 7

Effect of para-iodophenylboronic acid (PIBA) (5006) as an enhancer of a chemiluminescent reaction The experiment of Example 1 was repeated using PIBA in place of PBBA. Various dilutions of PIBA (Cookson Chemicals Ltd., Southampton, UK, 1 mg/ml stock in DMSO) in Tris buffer were used. Table 8 shows the effect PIBA has on the signal:background ratio of a chemiluminescent reaction measured after 1 minute.

TABLE 8

4-Iodophenylboronic acid (PIBA) enhancement of the HRP-luminol-peroxide reaction

| PIBA µg | Light emission at 1 minute Background | Signal | Signal:Background Ratio |
|---|---|---|---|
| 0 | 15,016 | 91,665 | 6.1 |
| 0.01 | 12,862 | 78,419 | 6.1 |
| 0.1 | 13,221 | 74,487 | 7.1 |
| 1 | 10,282 | 324,312 | 31.5 |
| 10 | 5,517 | 540,760 | 98 |
| 20 | 3,837 | 135,065 | 35.2 |

EXAMPLE 8

Use of an organoboron enhancer in a chemiluminescent assay for a) peroxide and b) luminol a) Effect of 4-biphenylboronic acid on a chemiluminescent assay for peroxide The assay reagent consisted of the following reagents: 10 µl 4-biphenylboronic acid (1:20 dilution of a 1 mg/ml stock in DMSO), 10 µl horseradish peroxidase (1:500,000 dilution of a 1 mg/ml stock Type VIA in 0.1 mol/l Tris buffer pH 8.6) and 100 µl luminol (0.025 g/l in 0.1 mol/l Tris buffer pH 8.6). These were mixed together and the light emission measured. A 10 µl sample of a hydrogen peroxide solution (dilutions of a stock, 31 µl 30% w/v hydrogen peroxide/ml in Tris buffer) was added, the contents of the assay tube mixed and the light emission recorded. The results are summarised in Table 9.

From Table 9 it can be seen that there was a dose-dependent increase in light output up to 2.4 µmoles of peroxide.

TABLE 9

Enhanced chemiluminescent assay for peroxide

| Hydrogen peroxide µmoles | Light emission at 5 minutes |
|---|---|
| 0 | 525 |
| 0.00024 | 659 |
| 0.0024 | 1,500 |
| 0.024 | 40,682 |
| 0.24 | 584,638 |
| 2.4 | 620,551 |
| 24 | 339,291 | b) Effect of 4-biphenylbornic acid on a chemiluminescent assay for luminol

The assay reagent consisted of the following reagents: 10 µl 4-biphenylboronic acid (1:20 dilution of a 1 mg/ml stock in DMSO), 10 µl horseradish peroxidase (1:500,000 dilution of a 1 mg/ml stock Type VIA in 0.1 mol/l Tris buffer pH 8.6) and 100 µl hydrogen peroxide solution (31 µl 30% w/v hydrogen peroxide diluted in 100 ml Tris buffer). These were mixed together and the light emission measured. A 10 µl sample of a luminol solution (dilutions of a 0.25 g/l in 0.1 mol/l Tris buffer pH 8.6 stock) was added, the contents of the assay tube mixed and the light emission recorded. The results are summarised in Table 10.

From Table 10 it can be seen that there was a dose-dependent increase in light output at all concentrations of luminol tested.

TABLE 10

Enhanced chemiluminescent assay for luminol

| Luminol μmoles | Light emission at 10 minutes |
|---|---|
| 0 | 54 |
| 0.00125 | 145 |
| 0.0125 | 620 |
| 0.125 | 5,161 |
| 1.25 | 55,873 |
| 12.5 | 358,184 |
| 125 | 834,089 |

EXAMPLE 9

Effect of 4-(2-carboxyethenyl)phenylboronic acid (CPA) (5007) as an enhancer of a chemiluminescent reaction

The experiment of Example 1 was repeated using CPA in place of PBBA. Various dilutions of CPA (Cookson Chemicals Ltd., Southampton, UK, 0.01–20 μg in 1 mg/ml Tris buffer, pH 8.6) were used. Table 11 shows the effect CPA had on the light output (signal) and signal to background ratio of a chemiluminescent reaction measured using an Amerlite microplate reader (Kodak Clinical Diagnostics, Amersham, UK).

TABLE 11

| CPA (μg) | Signal (with HRP) | Signal (no HRP) | Signal: Background ratio |
|---|---|---|---|
| 0 | 0.37 | 0.088 | 4.2 |
| 0.01 | 0.41 | 0.094 | 4.4 |
| 0.02 | 0.46 | 0.09 | 5.1 |
| 0.05 | 0.68 | 0.09 | 7.6 |
| 0.1 | 1.23 | 0.09 | 14.2 |
| 0.2 | 2.37 | 0.08 | 28.2 |
| 0.5 | 4.57 | 0.07 | 63.4 |
| 1.0 | 5.58 | 0.06 | 93.0 |
| 10 | 2.49 | 0.02 | 124.9 |
| 20 | 0.88 | 0.003 | 43.9 |

I claim:

1. A method of increasing the light output and/or signal:background ratio of light output from a chemiluminescent reaction of a dihydrophthalazinedione (DPD), a peroxidase enzyme catalyst and an oxidant, said method comprising the step of carrying out said chemiluminescent reaction in the presence of an enhancer comprising a compound selected from the group consisting of compounds of formula (I)

in which the R groups are the same and each is selected from the group consisting of hydrogen, n-butyl, 4'-chlorophenyl and 3',5'-dichlorophenyl; or the Rs together are O,O-propylene (thereby forming with the boron atom, a cyclic ether);

W is selected from the group consisting of hydrogen, methyl, methoxy, hydroxy and chloro;

X is selected from the group consisting of hydrogen, chloro, amino and nitro;

Y is selected from the group consisting of hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl;

Z is selected from the group consisting of hydrogen, 5-chloro, 5-bromo, 5-(3'-trifluorormethyl)phenylazo and 6-chloro; or W and X together may represent a fused benzene ring and X and Y together may represent a fused benzene ring substituted by hydroxy in the 6-position of the naphthalene ring numbering, provided that (1) when each R is hydrogen:
  (a) W, X, Y, Z are each hydrogen; or
  (b) W, X and Z are each hydrogen and Y is selected from the group consisting of iodo, bromo, chloro, trimethylsilyl, phenoxy, phenyl, 4'-chloroanilino, methyl, 4'-boronylphenyl and 2'-carboxyethenyl; or
  (c) W and Z are each hydrogen and:
    (i) X and Y together represent a fused benzene ring substituted by hydroxy in the 6-position of the naphthalene ring numbering; or
    (ii) X is either nitro or chloro and Y is chloro; or
    (iii) X is nitro and Y is carboxy; or
  (d) W, Y and Z are each hydrogen and X is amino, chloro or nitro; or
  (e) W and X together represent a fused benzene ring and Y and Z are each hydrogen; or
  (f) X and Y are each hydrogen and:
    (i) W is methoxy and Z is 5-bromo; or
    (ii) W is hydroxy and Z is 5-(3'-trifluoromethyl)phenylazo; or
    (iii) W is methyl and Z is hydrogen; or
  (g) W is chloro, X is chloro and Y and Z are each hydrogen; or
  (h) W and Y are each chloro, X is amino and Z is 6-chloro;

(2) when each R is n-butyl, W, X and Z are each hydrogen and Y is bromo or 4'-bromophenyl;

(3) when each R is 4'-chlorophenyl, W, X and Z are each hydrogen and Y is chloro;

(4) when each R is 3',5'-dichlorophenyl, W and Y are each hydrogen, X is chloro and Z is 5-chloro; and (5) when the Rs together represent O,O-propylene, X, Y and Z are each hydrogen;

and the compounds bis(catechol) borate, boroglycine, pentaerythritol borate, 4-(3'-borono-4'-hydroxyphenylazo) benzoic acid, diphenylisobutoxyborane, diphenylboronic anhydride and dimethylphenylboronic acid.

2. A method according to claim 1, wherein the enhancer is para-iodophenylboronic acid, para-bromophenylboronic acid, 4-biphenylboronic acid, 4-(trimethylsilyl) benzeneboronic acid, 2-hydroxy-5-[(3'-trifluoromethyl) phenylazo]benzeneboronic acid, boroglycine, 4-chloro-3-nitrophenylboronic acid, 4-chlorophenylboronic acid, 4-(2'-carboxyethenyl)phenylboronic acid, 4-(4'-bromophenyl) phenyl-di-n-butoxyborane, 4-chlorophenyl-di(4'-chlorophenoxy)borane, 4,4'-bis(phenylboronic acid), diphenylboronic anhydride, 4-(4'-chloroanilino) phenylboronic acid or 4-bromophenyl-di-n-butoxyborane.

3. A method according to claim 1, wherein the peroxidase enzyme is free or conjugated to a ligand and the presence or amount of the peroxidase is determined from the presence or amount of light output.

4. A method according to claim 1, wherein the peroxidase is horseradish peroxidase.

5. A method according to claim 4, wherein the horseradish peroxidase is in the form of a basic isoenzyme.

6. A method according to claim 1, wherein the oxidant is hydrogen peroxide.

7. A method according to claim 1, wherein the DPD is luminol.

8. A method according to claim 1, wherein the chemiluminescent reaction is carried out at a pH of from 7.5 to 9.

9. A method according to claim 1, wherein the peroxidase enzyme is conjugated to a ligand and the presence or amount of the peroxidase is determined from the presence or amount of light output, the DPD is luminol, the peroxidase is horseradish peroxidase, the oxidant is hydrogen peroxide and the chemiluminescent reaction is carried out at a pH of from 7.5 to 9.

10. A method according to claim 9, wherein the horseradish peroxidase is in the form of a basic isoenzyme.

11. A method of diagnostic assay of a substance, wherein the presence or amount of said substance is related to the presence or amount of a reaction partner selected from the group consisting of a dihydrophthalazinedione (DPD), a peroxidase enzyme, an oxidant and an enhancer which together react in a chemiluminescent reaction, wherein the reaction is carried out, the light output is detected or measured and the presence or amount of the substance to be assayed is related to the light output, and wherein the enhancer comprises a compound selected from the group consisting of compounds of formula (I)

in which the R groups are the same and each is selected from the group consisting of hydrogen, n-butyl, 4'-chlorophenyl and 3',5'-dichlorophenyl; or the Rs together are O,O-propylene (thereby forming with the boron atom, a cyclic ether);

W is selected from the group consisting of hydrogen, methyl, methoxy, hydroxy and chloro;

X is selected from the group consisting of hydrogen, chloro, amino and nitro;

Y is selected from the group consisting of hydrogen, methyl, carboxy, chloro, bromo, iodo, phenyl, phenoxy, 4'-chloroanilino, 4'-boronylphenyl, 4'-bromophenyl, 2'-carboxyethenyl and trimethylsilyl;

Z is selected from the group consisting of hydrogen, 5-chloro, 5-bromo, 5-(3'-trifluoromethyl)phenylazo and 6-chloro; or W and X together may represent a fused benzene ring and X and Y together may represent a fused benzene ring substituted by hydroxy in the 6-position of the naphthalene ring numbering, provided that (1) when each R is hydrogen:
  (a) W, X, Y, Z are each hydrogen; or
  (b) W, X and Z are each hydrogen and Y is selected from the group consisting of iodo, bromo, chloro, trimethylsilyl, phenoxy, phenyl, 4'-chloroanilino, methyl, 4'-boronylphenyl and 2'-carboxyethenyl; or
  (c) W and Z are each hydrogen and:
    (i) X and Y together represent a fused benzene ring substituted by hydroxy in the 6-position of the naphthalene ring numbering; or
    (ii) X is either nitro or chloro and Y is chloro; or
    (iii) X is nitro and Y is carboxy; or
  (d) W, Y and Z are each hydrogen and X is amino, chloro or nitro; or
  (e) W and X together represent a fused benzene ring and Y and Z are each hydrogen; or
  (p) X and Y are each hydrogen and:
    (i) W is methoxy and Z is 5-bromo; or
    (ii) W is hydroxy and Z is 5-(3'-trifluoromethyl)phenylazo; or
    (iii) W is methyl and Z is hydrogen; or
  (g) W is chloro, X is chloro and Y and Z are each hydrogen; or
  (h) W and Y are each chloro, X is amino and Z is 6-chloro;

(2) when each R is n-butyl, W, X and Z are each hydrogen and Y is bromo or 4'-bromophenyl;

(3) when each R is 4'-chlorophenyl, W, X and Z are each hydrogen and Y is chloro;

(4) when each R is 3',5'-dichlorophenyl, W and Y are each hydrogen, X is chloro and Z is 5-chloro; and (5) when the Rs together represent O,O-propylene, X, Y and Z are each hydrogen; and the compounds bis(catechol) borate, boroglycine, pentaerythritol borate, 4-(3'-borono-4'-hydroxyphenylazo) benzoic acid, diphenylisobutoxyborane, diphenylboronic anhydride and dimethylphenylboronic acid.

12. The method of claim 11, wherein the substance to be assayed is horseradish peroxidase conjugated to a ligand, the DPD is luminol and the oxidant is hydrogen peroxide.

13. The method of claim 12, wherein the enhancer is 4-chloro-3-nitrophenylboronic acid, 4-chlorophenylboronic acid, 4-(4'-bromophenyl)phenyl-di-n-butoxyborane, 4-chlorophenyl-di(4'-chlorophenoxy)borane or p-bromophenylboronic acid.

14. A kit for use in a diagnostic assay comprising in separate containers:

a chemiluminescent dihydrophthalazinedione (DPD);

a peroxidase enzyme catalyst; and an enhancer which increases the signal:background ratio of light output, wherein said enhancer is any one of the enhancers of claim 1.

15. A kit according to claim 14, wherein the enhancer is para-iodophenylboronic acid, para-bromophenylboronic acid, 4-biphenylboronic acid, 4-(trimethylsilyl) benzeneboronic acid, 2-hydroxy-5-[(3'-trifluoromethyl)phenylazo]benzeneboronic acid, boroglycine, 4-chloro-3-nitrophenylboronic acid, 4-chlorophenyl-boronic acid, 4-(2'-carboxyethenyl)phenylboronic acid, 4,4'-(bromophenyl)phenyl-di-n-butoxyborane, 4-chlorophenyl-di-(4'-chlorophenoxy)borane, 4,4'-bis(phenylboronic acid), diphenylboronic anhydride, 4-(4'-chloroanilino) phenylboronic acid or 4-bromophenyl-di-n-butoxyborane.

16. A kit according to claim 14, wherein the peroxidase is conjugated to a ligand.

17. A kit according to claim 14, wherein the peroxidase is horseradish peroxidase.

18. A kit according to claim 14, further comprising an oxidant.

19. A kit according to claim 18, wherein the oxidant is hydrogen peroxide.

20. A kit according to claim 14, wherein the DPD is luminol.

* * * * *